US008917312B1

(12) United States Patent
Gleason et al.

(10) Patent No.: US 8,917,312 B1
(45) Date of Patent: Dec. 23, 2014

(54) SYSTEM AND METHOD FOR DETECTING OPTICAL DEFECTS IN TRANSPARENCIES

(75) Inventors: Michael P. Gleason, Edwardsville, IL (US); Daniel E. Pulcher, St. Charles, MO (US); Douglas E. Reed, Washington, MO (US); Anthony C. Roberts, O'Fallon, MO (US); Matthew M. Thomas, Maryland Heights, MO (US)

(73) Assignee: The Boeing Company, Chicago, IL (US)

( * ) Notice: Subject to any disclaimer, the term of this patent is extended or adjusted under 35 U.S.C. 154(b) by 1474 days.

(21) Appl. No.: 12/394,012

(22) Filed: Feb. 26, 2009

(51) Int. Cl.
*G06K 9/00* (2006.01)

(52) U.S. Cl.
USPC .............................. 348/36; 382/141; 382/142

(58) Field of Classification Search
USPC ........... 349/61, 112; 356/239.1; 362/471, 511
See application file for complete search history.

(56) References Cited

U.S. PATENT DOCUMENTS

| | | | |
|---|---|---|---|
| 4,310,242 A * | 1/1982 | Genco et al. | 356/128 |
| 4,461,570 A * | 7/1984 | Task et al. | 356/239.1 |
| 5,343,288 A * | 8/1994 | Cohen et al. | 356/239.1 |
| 5,479,276 A * | 12/1995 | Herbermann | 349/5 |
| 6,001,486 A * | 12/1999 | Varaprasad et al. | 428/428 |
| 7,365,838 B2 * | 4/2008 | Jones | 356/239.1 |
| 2006/0092276 A1 * | 5/2006 | Ariglio et al. | 348/132 |
| 2009/0251917 A1 * | 10/2009 | Wollner et al. | 362/543 |

OTHER PUBLICATIONS

ISRA Vision, "Fully Automated Final Optical Inspection of Automotive Glass: Inspects for Straying, Distorting and Absorbing Defects With One Modular System", available at <http://www.isravision.com/likecms.php?site=index. html&dir=isra&nav=193&siteid=&entryid=> last visited on Feb. 9, 2009.

ISRA Vision, "A Unique System That Inspects Glass Sheets for Every Processing Stage in Any Formation Without Interruption and in a Highly Flexible Manner", available at <http://www.isravision.com/likecms.php?site=index. html&dir=isra&nav=193&siteid=&entryid=> last visited on Feb. 9, 2009.

American Society for Testing and Materials, ASTM F733-90(2003) "Standard Practice for Optical Distortion and Deviation of Transparent Parts Using the Double-Exposure Method," available at <http://www.astm.org/Standards/F733.htm> last visited on Feb. 9, 2009.

\* cited by examiner

*Primary Examiner* — Tung Vo
*Assistant Examiner* — Obafemi Sosanya

(57) ABSTRACT

An optical defect detection system is provided for recording an image of a transparency for detecting optical defects therein. The transparency may be formed with a contour. The defect detection system may comprise a light source, a diffuser and an image recording device for recording images of the transparency. The light source is configured to emit light and may be positioned adjacent one of the sides of the transparency. The image recording device may be positioned on a side of the transparency opposite the diffuser. The diffuser may be contoured complementary to the contour of the transparency and may be positioned between the light source and the transparency.

20 Claims, 5 Drawing Sheets

SYSTEM AND METHOD FOR DETECTING OPTICAL DEFECTS IN TRANSPARENCIES

CROSS-REFERENCE TO RELATED APPLICATIONS (Not Applicable)

STATEMENT RE: FEDERALLY SPONSORED RESEARCH/DEVELOPMENT (Not Applicable)

FIELD

The present disclosure relates generally to inspection systems and, more particularly, to a system for detecting optical defects in transparencies.

BACKGROUND

Transparencies are used in a variety of different applications including vehicular applications such as in marine, land, air and/or space vehicles and in non-vehicular applications such as in buildings and other stationary structures. In vehicular applications such as in commercial aircraft, transparencies may be mounted along the aircraft cabin and around the aircraft flight deck and may include windshields and other forward, side and overhead windows. Transparencies may be formed of glass and polymeric materials or as laminated combinations of glass and polymeric materials. Polymeric materials for transparencies may include, without limitation, acrylic and polycarbonate compositions.

When fabricating a transparency of polycarbonate material, certain optical defects may occur during the forming process. For example, carbon particulates may occur during the formation of a polycarbonate transparency and may appear as relatively small black spots embedded within the transparency. When viewed through the transparency, an embedded carbon particulate may be misinterpreted as a long-distance object. Other optical defects may occur in the transparency such as runs and sags which can also affect the quality of the transparency.

Included in the prior art are several methods for inspecting transparencies for optical defects. For example, certain aircraft transparencies such as a canopy may be manually-inspected by looking upwardly though the canopy searching for defects and using the sky as a background. This inspection technique requires generally clear (e.g., non-cloudy) atmospheric conditions in order to provide a homogenously lit background against which an inspector can view the entirety of the transparency. As may be expected, this inspection technique may result in significant aircraft downtime while waiting for the appropriate atmospheric conditions.

Although camera-driven methods have been developed in the automotive industry for automating inspection of transparencies, automated camera methods may lack the resolution required for aerospace transparencies. For example, automated methods used in the automotive industry are typically directed toward high-speed inspection of a transparency on a production line wherein the size of allowable defects is typically larger than the allowable defect size (e.g., 0.030 inch) of aerospace transparencies. In this regard, the resolution at which an automotive transparency is inspected is sacrificed in the interest of high-volume production.

Furthermore, inspection methods used in the automotive industry are typically directed toward transparencies having relatively slight curvatures as compared to aircraft transparencies such as aircraft canopies and windshields which may have more complex curves and which may be of smaller radius. In addition, the cross-sectional layup of an aircraft transparency such as an aircraft windshield is generally more complex than an automotive transparency due to the higher strength requirements and increased thickness (e.g., up to 1 inch thick or larger) of an aircraft windshield which may be necessary for surviving bird strikes and handling structural loads.

As can be seen, there exists a need in the art for a system and method for detecting optical defects in a transparency that provides an automated means for recording images of the transparency in order to document the size and location of optical defects. The need to accurately quantify an optical defect (e.g., measure the defect size and document the location) in an aircraft transparency is desirable due to the relatively high cost of replacing an aircraft windshield as compared to the cost of replacing an automotive windshield.

Furthermore, there exists a need in the art for a system and method for high resolution imaging of the transparency to enable detection of defects of relatively small size (e.g., having a width as small as about 0.010 inch or smaller). Additionally, there exists a need in the art for a system and method for detecting optical defects in a transparency in a high-speed manner in order to reduce inspection time. Finally, there exists a need in the art for a system for detecting optical defects that is simple in construction, low in cost and which is adaptable for inspecting a wide range of transparency configurations.

BRIEF SUMMARY

The above-noted needs associated with inspection of transparencies are specifically addressed and alleviated by the present disclosure which provides an optical defect detection system for recording detailed images of a transparency such that optical defects in the transparency may be detected. The defect detection system may be adapted to record images of transparencies having a contoured or curved shape although the defect detection system may be used to inspect slightly curved or planar transparencies. Advantageously, the defect detection system is configured to allow for detection of optical defects down to a relatively small size (e.g., 0.010 inch) through the use of a diffuser for uniformly illuminating the transparency.

The defect detection system may comprise a light source, the diffuser and an image recording device such as a camera. The light source and diffuser may be positioned on one side of the transparency to provide a homogeneously illuminated background against which a viewing portion (i.e., transparent portion) of the transparency may be inspected by the imaging recording device located on an opposite side of the transparency. For transparencies having a transparency frame, the viewing portion comprises the clear or transparent portion of the transparency that is unblocked by the transparency frame. Advantageously, the defect detection system allows for screening out of transparencies that may have optical defects to prevent installation thereof on an aircraft or on other vehicles or in other structures.

The diffuser may be contoured or curved into a shape that is complementary to the contour or shape of the transparency. Likewise, the light source may be configured in an arrangement that is complementary to the shape of the diffuser to provide a uniform or homogeneous distribution of light to the diffuser. The light source may be provided as one or more lighting elements such as fluorescent lamps or other lighting elements configurations. In this regard, the light source may be provided in any suitable arrangement that emits light which is at least partially incident upon the diffuser. The light source and diffuser may be configured to limit the amount of heat output that may be transmitted to the diffuser and/or to the transparency.

The light source may be configured as a plurality of elongate fluorescent tubes or lamps arranged in parallel relation to one another and positioned in an arcuate pattern complementary to the shape or curve of the diffuser. However, it should be noted that the light source is not limited to the use of conventional elongate fluorescent lamps and may be configured in any suitable configuration. For example, the light source may be configured as an array of incandescent bulbs of any size, shape or configuration and/or as an array of light emitting diodes (LEDs) or other light source configurations. Ideally, the light source may be configured to provide a substantially uniform pattern of light for illuminating the diffuser. The output of the light source is preferably of high luminance but also preferably has a relatively low heat output in order to avoid excessive heating of the diffuser and/or transparency.

The diffuser is preferably positioned between the light source and the transparency and may be configured to diffuse or distribute light substantially uniformly throughout the diffuser to provide a homogeneous background against which the transparency may be imaged by the image recording device. As was indicated above, the diffuser is preferably contoured complementary to a contour of the transparency. For example, if the transparency is an aircraft windshield and/or an aircraft canopy having one or more curves, the diffuser is preferably formed complementary to the transparency such that the viewing portion of the transparency is substantially uniformly backlit by the combination of the light source and the diffuser.

The diffuser may be formed of a material that transmits a suitable range of visible light such that the light is uniformly diffused or distributed without the occurrence of shadows, hotspots or bright spots in the diffuser. In one embodiment, the diffuser may be formed of an acrylic sheet such as Plexiglas sheet which may be formed at a desired contour by simply bending the sheet into the desired shape and fixing the sheet within a diffuser frame. However, in order to reduce or eliminate springback of the diffuser toward its original flat or planar condition, the diffuser may be heated to a temperature below the melting point (e.g., 200 degrees Fahrenheit for 5 minutes) after the diffuser is formed into the desired contour after which the diffuser may be allowed to cool. The diffuser may also be fixedly mounted to a housing in order to maintain the shape or contour of the diffuser. Additionally, the diffuser may be installed within the diffuser frame in order to reduce springback.

The diffuser may be formed of any suitable material having sufficient light transmittance characteristics to allow illumination or backlighting of the transparency. In one embodiment, the diffuser may be configured to transmit a range of approximately 25-75% of visible light. In a preferable embodiment, the diffuser may be configured to transmit about 50% of the light that is emitted by the light source although the diffuser may be selected to transmit any amount of light that allows for sufficient illumination or backlighting of the transparency.

Although the diffuser may be formed of any suitable polymeric or non-polymeric (e.g., glass) material, due to the need to form the diffuser in a shape that is complementary to the contour of the transparency, the diffuser is preferably formed of a sheet of polymeric material. As indicated above, the diffuser may be formed of acrylic material such as that which is commercially known as Plexiglas. However, the diffuser may be fabricated of any suitable material capable of transmitting a sufficient quantity of light and having suitable diffusive characteristics including, without limitation, glass, acrylic, and/or polycarbonate compositions.

The image recording device may be configured as a panoramic camera which may be stationary or which may be movable. For example, the image recording device may be rotatable about an axis of rotation. The image recording device may be positioned on a side of the transparency opposite the diffuser. The image recording device preferably has a sufficiently high resolution to enable recording of detailed images of the transparency to allow detection of optical defects having a width at least as small as 0.010 inch or smaller. Furthermore, the image recording device may be fitted with a suitable lens to facilitate scanning of the entirety of the transparency. For example, the image recording device may be fitted with a wide-angle lens (e.g., fisheye lens) of any suitable focal length to enable capturing of the perimeter areas of the transparency. Such lenses may have a hemispherical field of view and/or a vertical field of view. The field of view may encompass the extreme upper and lower edges of the viewing portion of the transparency although the lens may have a field of view that encompasses a portion of the viewing portion and therefore may require movement (e.g., translation and/or rotation) of the image recording device in order to facilitate the recording of images of the viewing portion that fall outside of the field of view of the lens.

The field of view of the lens may also encompass the extreme lateral edges (e.g., opposing lateral sides) of the viewing portion of the transparency although the field of view may encompass a portion of the viewing portion between the opposing lateral sides. As mentioned above, the image recording device may be movably mounted in order to facilitate capturing of images of the viewing portion which fall outside of the field of view of the lens. Toward this end, the image recording device may be configured as a panoramic camera that is movable. For example, the image recording device may be translatable in any number of directions such as along a vertical and/or horizontal direction to enable capturing of the entirety of the viewing portion. The image recording device may be rotatable about at least one axis of rotation. In this regard, the image recording device may be rotatable about an axis of rotation which facilitates the recording of the viewing portion between and including the opposing lateral edges of the transparency. In this manner, the entirety of the viewing portion may be recorded during rotation of the image recording device including areas between and including the upper and lower edges and areas between and including the lateral edges of the transparency. Even further, the image recording device may be rotatable about other axes of rotation such as about a horizontal axis of rotation to facilitate the capturing of images that are normally outside of the vertical field of view when the lens is stationary.

The image recording device may be provided in a resolution that facilitates recording or optical defects that are of relatively small size or which have a relatively small cross-sectional width. For example, the image recording device may be capable of recording defects having a width at least as small as about 0.010 inch over an entirety of the viewing portion of the transparency when viewing the defect along a direction with which the transparency is being imaged. In one embodiment, the image recording device (e.g., a panoramic camera) may have a vertical resolution of up to at least about 9,000 pixels for a 175 degree vertical view of view and a horizontal resolution of up to at least about 65,000 pixels for a 360 degree rotation of the image recording device. However, the horizontal resolution is dependent upon the extent of angular rotation of the image recording device about the axis of rotation. For example, if rotation of the image recording device about the axis of rotation is limited to 225 degrees, then the horizontal resolution may be proportionally reduced such as to a horizontal resolution of between about 10,000-15,000 pixels. However, the image recording device may be provided with any suitable amount of resolution for recording detailed images of the entirety of the transparency.

In order to enhance the amount of light that is produced by the light source for illuminating the diffuser, the defect detection system may further include a reflector which may be positioned on a side of the light source opposite the diffuser. The reflector may be configured as a sheet of fabric, paper, plastic or metallic material or as any other suitable composition sufficient for reflecting light emitted by the light source in order to maximize the illumination of the diffuser. The reflector may also be comprised of layers of paint, tape, or other materials including coatings of any color, configuration or composition. In one embodiment, the reflector may be positioned between the lighting elements (e.g., fluorescent lamps) and light fixtures which are associated with each of the lighting elements. The reflector may be fixedly secured to the lighting elements and/or to the housing. However, the reflector may be incorporated into the lighting elements as an integral component thereof although the reflector may be mounted in any other suitable manner.

As mentioned above, the defect detection system may further include the housing which may be adapted for mounting the light source, the diffuser and/or the reflector in fixed relation to one another. However, the light source, diffuser and reflector may be configured to be adjustable relative to one another in order to provide a degree of flexibility with regard to substituting different lighting elements having different light output and heat output characteristics. For example, the housing may be configured to accommodate variations in size (e.g., length), shape and configuration of the fluorescent lamps in order to achieve different levels of brightness or intensity of the diffuser.

The defect detection system may further include a transparency fixture which may be configured as a separate fixture independent of the housing. The transparency fixture may be configured to mount the transparency and the image recording device in fixed relation to one another. The transparency fixture may optionally be mounted on casters, wheels, rollers or other devices to facilitate transportability of the transparency fixture. The transparency may preferably be mounted on casters in order to reduce or reduce or eliminate extraneous movement of the transparency fixture such as during imaging of the transparency. Likewise, the housing may be also fitted with wheels or rollers to facilitate transportability or movement of the detection fixture such as within an inspection facility.

The transparency fixture may be configured to mount the transparency relative to the image recording device so as to minimize variations in distance between the lens and the upper edge of the transparency as compared to the distance between the lens and the lower edge of the transparency. For example, the image recording device may be positioned such that the lens is positioned at a mid-height of the transparency. The transparency may also be positioned relative to the image recording device so as to minimize variations in distance between the lens and the opposing lateral edges of the transparency. For embodiments wherein the image recoding device is rotatable about the axis of rotation, the transparency may be positioned to minimize variations in the distance from the lens to the transparency throughout the rotational path of the image recording device. By equalizing the distance between the lens and the transparency throughout the rotational path, the average resolution at each location on the transparency is maximized and focusing problems may be minimized.

Importantly, the image recording device, the transparency and the diffuser are preferably positioned such that any vector that projects or extends from the image recording device (i.e., extends from the lens) and which passes through any point on the viewing portion will intersect or strikes the diffuser. A vector that projects or extends from the image recording device represents a direction along which the viewing portion of the transparency is viewed from the lens. For a stationary (i.e., non-moving) image recording device, a vector that extends from the lens falls within the angular field of view of the lens. By moving the image recording device when recording images, the field of view may be increased. For example, by rotating the image recording device about a vertical axis of rotation while recording images, the horizontal field of view of the lens is increased. Similarly, by rotating the image recording device about a horizontal axis of rotation, the vertical field of view may be increased. Translation of the image recording device such as vertical or horizontal movement results in a similar increase in the field of view.

As was earlier indicated, the diffuser is preferably substantially uniformly illuminated such that any point on the viewing portion is suitably backlit by the diffuser when viewed through the image recording device. The image recording device, in one embodiment, may be configured as an automated, high-resolution, high-speed digital panoramic camera that is rotatable about the axis of rotation and which facilitates the ability to detect and document the location and size of optical defects or other irregularities that may exist in the transparency.

The technical effects of the defect detection system include an improvement in the reliability, speed and accuracy with which transparencies may be inspected for optical defects as compared to prior art manual inspection methods. In addition, the defect detection system provides a means for reliably detecting optical defects of relatively small size and means for recording at least the size and/or location of such optical defects. Furthermore, the defect detection system provides a means for recording images of a contoured or curved transparency in an automated manner by using a diffuser which may be shaped or contoured complementary to the transparency contour.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present invention will become more apparent upon reference to the drawings wherein like numbers refer to like parts throughout and wherein.

DETAILED DESCRIPTION

Referring now to the drawings wherein the showings are for purposes of illustrating preferred and various embodiments of the disclosure only and not for purposes of limiting the same, shown in the figures is an optical defect detection system 10 for recording one or more images of a transparency 104. The optical defect detection system 10 may include a detection fixture 12 which may include a diffuser 48 that may be contoured or shaped complementary to the geometry of the transparency 104. The transparency 104 may be mounted on a transparency fixture 70 which may be positionable in alignment with an imaging recording device 22 such as a panoramic camera 24. The imaging recording device 22 may be configured to record detailed (i.e., high resolution) images of a viewing portion 122 of the transparency 104.

Figure 1:
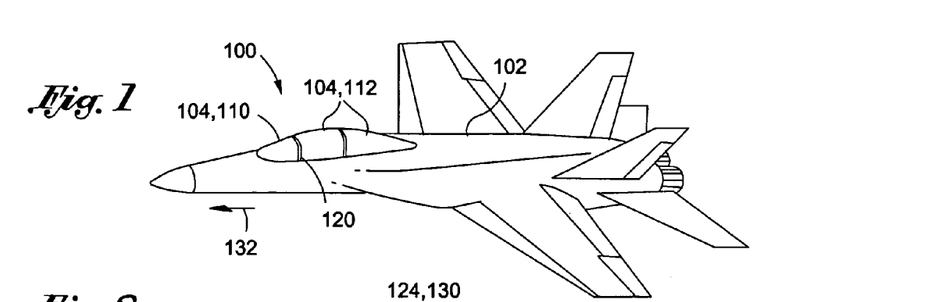
FIG. 1 is a perspective illustration of an aircraft having one or more transparencies.
Figure 4:
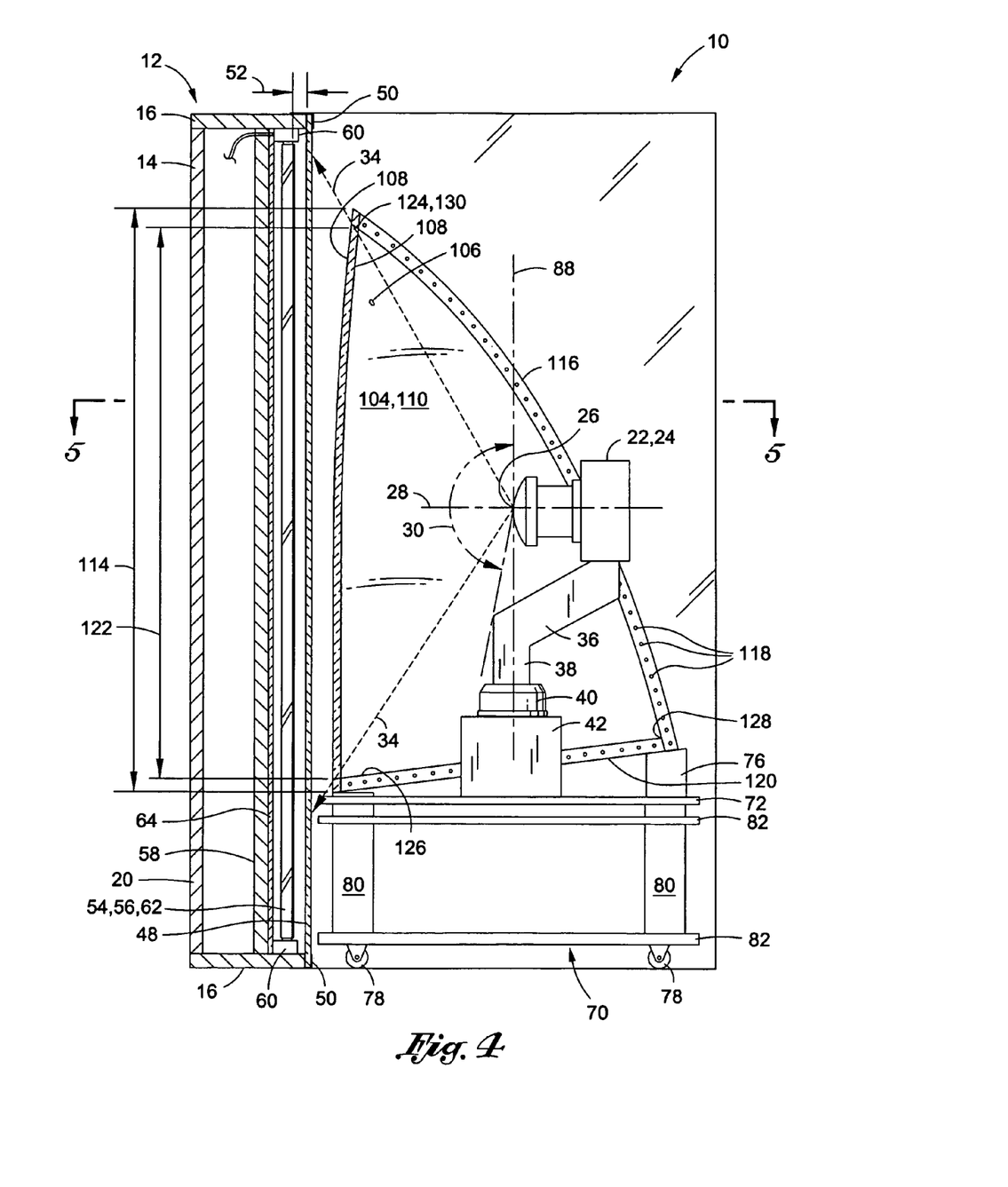
FIG. 4 is a side sectional illustration of the defect detection system and illustrating the relative positioning of the diffuser, the transparency and the image recording device.
Figure 5:
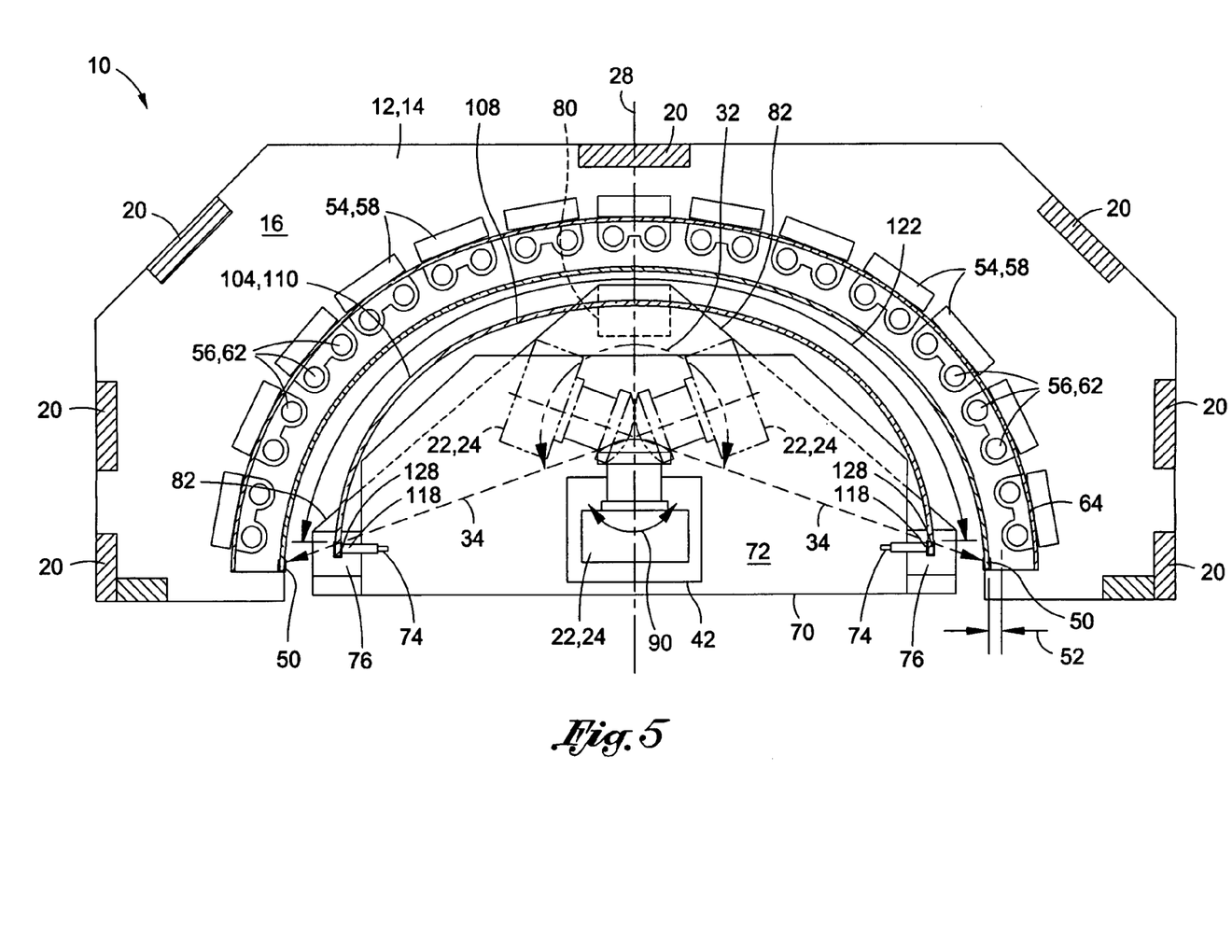
FIG. 5 is a top sectional illustration of the optical defect detection system taken along line 5-5 of FIG. 4 and wherein the image recording device is configured as a panoramic camera.

The transparencies 104 may comprise a transparent or relatively clear panel 16 as may be used in vehicular or in non-vehicular applications. For example, FIG. 1 illustrates an aircraft 100 having several transparencies 104 for which the defect detection system 10 may be employed for recording images of the transparencies 104 in order to detect optical defects 106. The aircraft 100 shown in FIG. 1 includes a fuselage 102 having a cockpit with one or more transparencies 104 such as a canopy 112 or a windshield 110 at a forward 132 end of the aircraft 100. The windshield 110 transparency 104 may include a transparency frame 116 having an aft arch member 120 for supporting the transparency 104. The windshield 110 transparency 104 may include a viewing portion 122 through which a pilot may view objects external to the windshield 110. In this regard, the viewing portion 122 comprises the clear or transparent portion of the transparency 104 that is unblocked by the transparency frame 116 as shown in FIGS. 4-5.

The defect detection system 10 as disclosed herein provides a means for detecting optical defects 106 such as, without limitation, carbon particulates that may be embedded within a polycarbonate layer of the windshield 110. It should be noted that the aircraft windshield 110 transparency 104 illustrated throughout the figures and as described herein is not to be construed as limiting other types of transparencies 104 for which the defect detection system 10 may be used for detecting defects 106. In this regard, the defect detection system 10 may be employed for recording images and detecting optical defects 106 in a wide variety of transparencies 104 for a variety of different applications. For example, the defect detection system 10 may be used for recording images of transparencies 104 in any marine, land, air and/or space vehicle as well as for recording images in transparencies 104 used in non-vehicular applications including window panels or glazing materials used in buildings and structures and in other assemblies or systems such as instruments, lighting assemblies, lenses and in any glassware and/or plastic or polymeric compositions where detection of optical defects 106 is desired.

Advantageously, the defect detection system 10 allows for inspection of transparencies 104 having a contoured or curved shape although transparencies 104 having a generally flat or planar configuration may be inspected using the defect detection system 10. For contoured or curved transparencies 104, the diffuser 48 and a light source 54 may be formed complementary to the contour of the transparency 104. For example, for the aircraft 100 windshield 110 and/or aircraft 100 canopy 112 having one or more curves as shown in FIG. 1, the diffuser 48 is preferably formed in a shape which mirrors the shape of the transparency 104 at a spaced distance from the transparency 104 such that the viewing portion 122 of the transparency 104 is substantially uniformly back lit by the combination of the light source 54 and the diffuser 48.

Referring generally to FIGS. 2-5, the light source 54 may be configured as an arrangement of one or more lighting elements 56 which may be configured to illuminate the diffuser 48. In this manner, light emitted by the light source 54 is substantially uniformly diffused or distributed throughout the diffuser 48 to provide uniformly-distributed background lighting behind the entire viewing portion 122 of the transparency 104. In addition, the light source 54 and diffuser 48 are preferably arranged such that the entirety of the viewing portion 122 is illuminated within the field of view of the image recording device 22. Optical defects 106 similar to that which is illustrated in exaggerated size in FIGS. 2-5 may be reliably detected by the defect detection system 10.

Referring briefly to FIGS. 4-5, the image recording device 22 may comprise a camera 24 such as the panoramic camera 24 mentioned above and which may include a wide-angle lens 26 (i.e., a fisheye lens) having a vertical field of view 30 that may encompass extreme upper and lower edges 124, 126 of the transparency 104 as illustrated by vectors 34 projecting or extending from the lens 26. However, the vertical field of view 30 of the image recording device 22 (i.e., of the lens 26) may be such that only a portion of the area between upper and lower edges 124, 126 is captured.

As indicated earlier, a vector 34 that projects or extends from the image recording device 22 represents a direction along which objects are viewed from the lens. A vector 34 that extends from the lens falls within the angular field of view of the lens. By moving (e.g., translating, rotating) the image recording device 22 when recording images, the field of view may be increased. For example, by rotating the image recording device 22 about a vertical axis of rotation 88 while recording images, the horizontal field of view 32 is increased. Similarly, by rotating the image recording device 22 about a horizontal axis of rotation (not shown), the vertical field of view 30 may be increased. Rotation of the image recording device 22 about other axes is also contemplated. Translation of the image recording device 22 such as vertical or horizontal movement of the image recording device 22 results in a similar increase in the field of view. For example, the transparency may be imaged by The image recording device 22 may have a horizontal field of view 32 that encompasses opposing lateral sides of the transparency 104 such as the extreme lateral edges 128 on each lateral side of the transparency 104 as illustrated by the vectors 34. Toward this end, the image recording device 22 may be rotatable about the axis of rotation 88 to enable recording of the entirety of the viewing portion 122 between the opposing lateral edges 128 of the transparency 104. By rotating the image recording device 22 about the axis of rotation 88, the image recording device 22 provides a vertical field of view 30 and a horizontal field of view 32 to enable detection of optical defects 106 between and including the physical extremes of the transparency 104.

Figure 2:
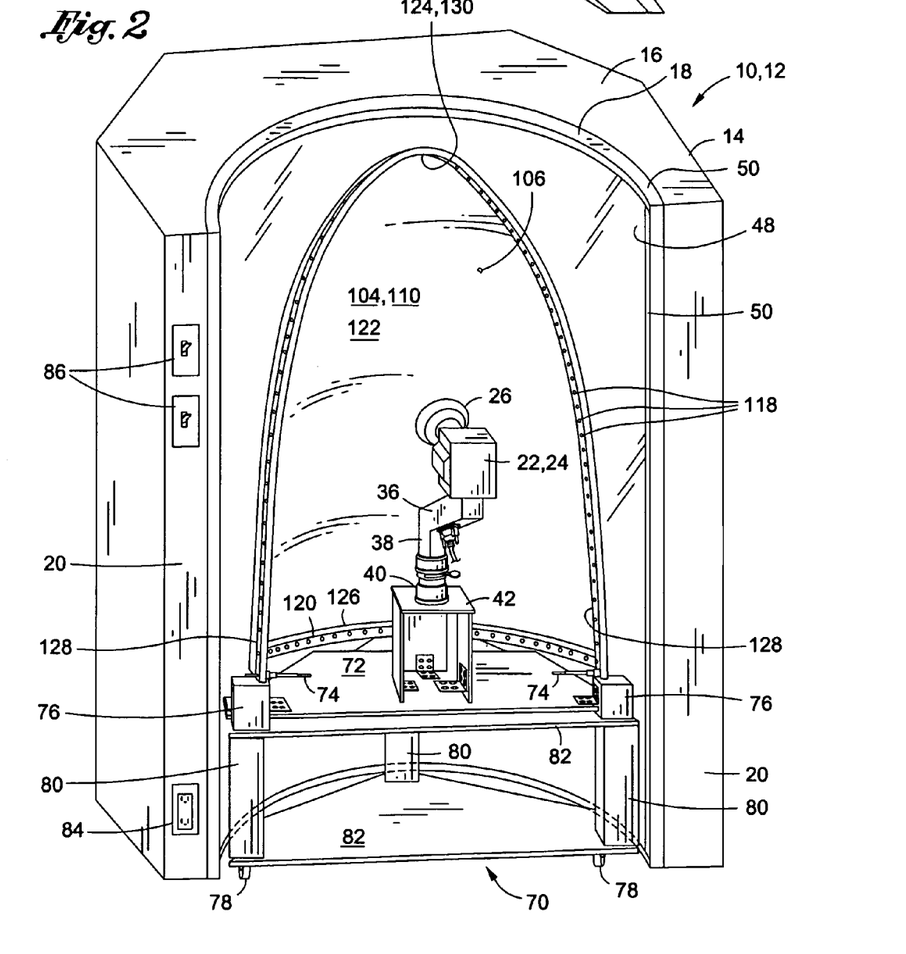
FIG. 2 is a perspective illustration of an optical defect detection system for recording and/or detecting optical defects in a transparency.
Figure 3:
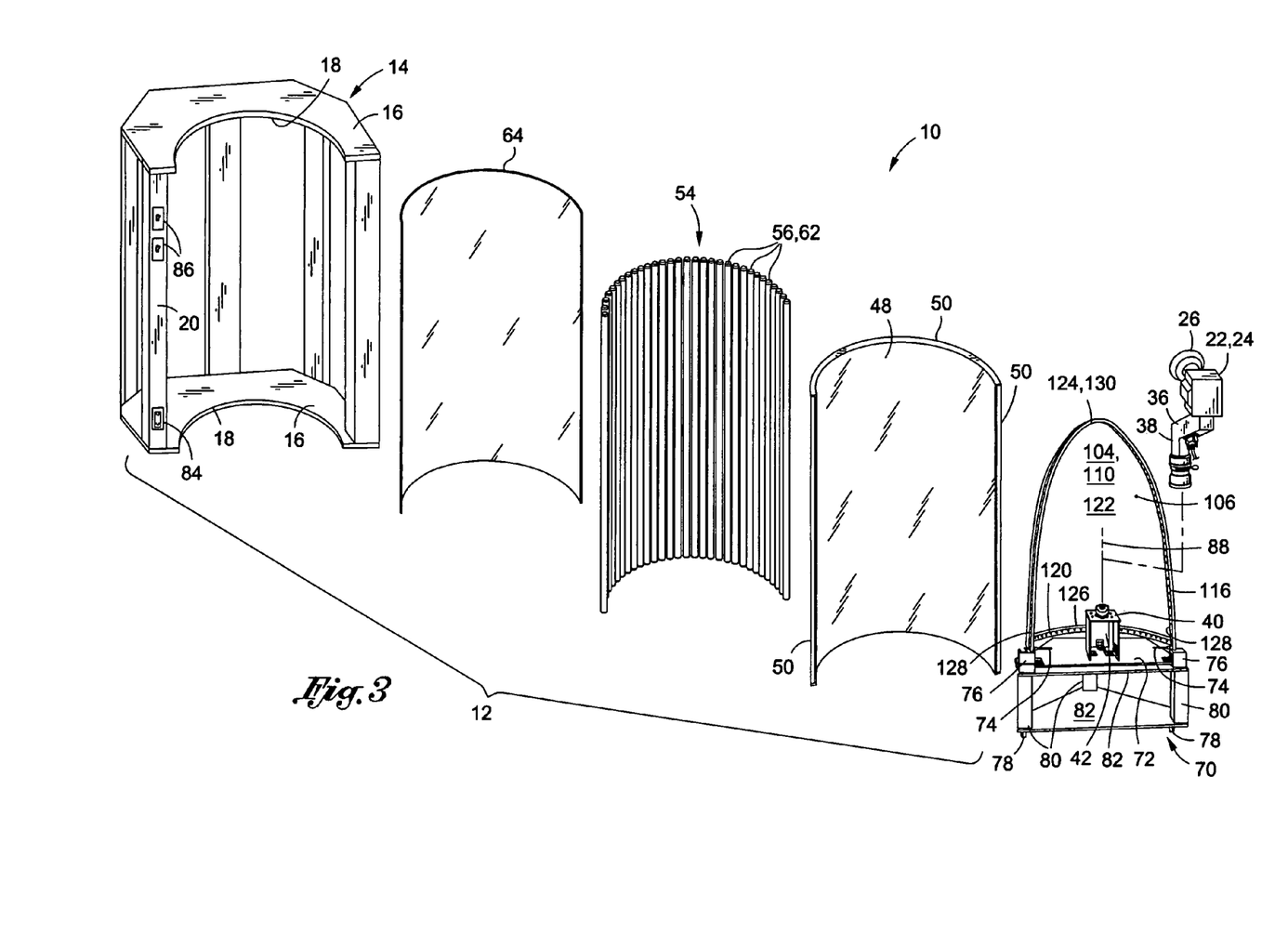
FIG. 3 is an exploded illustration of the defect detection system as shown in FIG. 2 and illustrating a transparency fixture to which an image recording device may be mounted and further illustrating a diffuser, a light source and a reflector which may be mounted within a housing.

Referring generally to FIGS. 2-5, shown is the optical defect detection system 10 comprising the light source 54, the diffuser 48 and the image recording device 22. The light source 54 is configured to emit light and, in this regard, may comprise any suitable illumination device capable of providing or emitting light for diffusion by the diffuser 48. For example, the light source 54 may be comprised of one or more incandescent and/or fluorescent lamps 62 or bulbs. As shown in FIG. 3, a plurality of fluorescent lighting elements 56 or fluorescent tubes may be arranged in an arcuate pattern and positioned in spaced, parallel relation to one another. However, the lighting elements 56 may be configured as any suitable device capable of emitting light without producing excessive heat that may otherwise damage the diffuser 48 and/or transparency 104.

Additionally, although incandescent bulbs and other light sources 54 such as light emitting diodes (LEDs) may be used for the light source 54, fluorescent tubes may be a preferred configuration due to their relatively high intensity or brightness (i.e., luminance), reduced heat output and extended operating life as compared to incandescent bulbs or lamps. Although shown in FIG. 3 as a plurality of elongate fluorescent lamps 62, the light source 54 may be fabricated or configured in a variety of alterative arrangements such as in an array of incandescent bulbs and/or LED's or as a combination of any other lighting elements 56 which may be provided as a single light source 54 or as a plurality of lighting elements 56.

Referring to FIGS. 3-5, the fluorescent lamps 62 may be mounted in a plurality of light fixtures 58 arranged in a vertical orientation. The light fixtures 58 may be fixedly mounted to the housing 14 of the detection fixture 12. Each one of the lighting elements 56 (i.e., fluorescent lamps 62) may be equidistantly spaced along the contour of the diffuser 48 to provide a uniformly distributed light output to the diffuser 48. Each light fixture 58 may be configured to mount one or more (e.g., a pair) of the fluorescent lamps 62 in upper and lower lamp holders 60 of each light fixture 58. In an embodiment, the light fixtures 58 may be configured as 120/277 Volt fixtures for powering 85-watt fluorescent lamps 62 each having a capacity of 5,500 lumens of fluorescent lighting. However, fluorescent lamps 62 of any voltage, current draw or lumen capacity may be used. The uniformly-spaced fluorescent lamps 62 provide a uniform distribution of light to the diffuser 48 as a background for recording images of the transparency 104. However, as was indicated above, any configuration of lighting element 56 may be used for illuminating the diffuser 48.

Referring still to FIGS. 3-5, the defect detection system 10 may include a reflector 64 which may be positioned adjacent the light source 54. As shown in FIGS. 4-5, the reflector 64 may be positioned between the light fixtures 58 and the fluorescent lamps 62. In this arrangement, the reflector 64 is positioned on a side of the lighting element 56 opposite the diffuser 48 such that the reflector 64 reflects light emitted by the light source 54. The light is preferably reflected in a direction toward the diffuser 48 in order to maximize the total amount of light that is provided to the diffuser 48. In this regard, the reflector 64 facilitates homogenous illumination of the diffuser 48 wherein light is substantially uniformly distributed throughout the diffuser 48.

Furthermore, the reflector 64 serves the diffuser 48 by reflecting light in a manner that eliminates the occurrence of shadows, bright spots and/or hot spots in the diffuser 48. The reflector 64 may be fixedly or temporarily mounted to the housing 14 of the detection fixture 12. The reflector 64 may be positioned behind the light source 54 and may extend between upper and lower panels 16 of the housing 14 as best seen in FIG. 4. In one embodiment, the reflector 64 may be comprised of a sheet of metallic material fixedly mounted to the light fixtures 58 and/or formed to match the contour of the diffuser 48 and/or the arcuate shape of the light source 54 as shown in FIG. 3. In addition, the reflector 64 is preferably disposed in slightly spaced relationship to the lighting elements 56 to maximize the amount of reflected light that may be directed toward the diffuser 48. As may be appreciated, the reflector 64 may comprise any suitable reflecting material and may be configured in a variety of different arrangements including, but not limited to, a sheet of paper, plastic, metal or combinations thereof. In addition, the reflector 64 may be configured as a layer of paint in any suitable reflective color or finish. Furthermore, the reflector 64 may be simply comprised of a reflective coating or treatment applied to the light fixtures 58 and/or to a backing (not shown) disposed on a side 108 of the transparency 104 opposite the diffuser 48.

Referring still to FIGS. 3-5, shown is the diffuser 48 which is preferably interposed between the light source 54 and the transparency 104 and which may be contoured or shaped complementary to the transparency 104 to facilitate uniform backlighting thereof when viewed or imaged by the image recording device 22. Toward this end, the diffuser 48 may be fabricated of a suitable glass and/or polymeric material having a desired transmittance. The diffuser 48 may be heat treated in order to avoid fissures and/or cracks when forming the diffuser 48 into relatively small radii of curvature as may be required to conform to certain transparencies 104 having tight curvatures such as aircraft 100 canopies 112 and windshields 110 of small, high-speed aircraft 100. Heat treating the diffuser 48 prior to forming at the desired radius may also be necessary to prevent springback or creep of the diffuser 48 towards a flatter or larger radius.

Toward this end, the diffuser 48 may be provided with a diffuser frame 50 to maintain the curvature of the diffuser 48. The diffuser frame 50 may be of any construction including, but not limited to, metallic and/or polymeric construction although other materials may be used to form the diffuser frame 50 to maintain the curvature of the diffuser 48. In this regard, it is contemplated that the diffuser 48 may be fastened to cutouts 18 formed in each of the upper and lower panels 16 of the housing 14 in order to maintain the position and curvature of the diffuser 48.

Although shown as having a singly curved configuration, the diffuser 48 may be formed in a complex or contoured shape. For example, for inspecting a curved aircraft 100 canopy 112 such as that shown in FIG. 1, the diffuser 48 may be formed in a compound curved shape and, depending upon the minimum allowable bend radius for a given material composition and thickness, may require heat-treating to form the diffuser 48 into the small radii of the canopy 112.

The diffuser 48 may be configured as a sheet of material such as polymeric material capable of transmitting a desired percentage of light. For example, the diffuser 48 may be configured to transmit about 25-75% of the light such as the light that is emitted by the light source 54 and/or reflected by the reflector 64. In a further embodiment, the diffuser 48 may be configured to transmit at least about 50% of the light emitted by the light source 54 and/or reflected by the reflector 64. However, the diffuser 48 may be configured to transmit any amount of light.

Regarding material for the diffuser 48, a thermoplastic transparent sheet of material such as acrylic may be used although other polymeric compositions including, but not limited to, polycarbonate materials may be used. Even further, it is contemplated that the diffuser 48 may be fabricated of glass having the appropriate diffusion properties for uniformly distributing light throughout the area of the diffuser 48. However, polymeric compositions may be preferred due to the relative ease of forming polymeric sheets into complex or contoured shapes. In this regard, the diffuser 48 may be fabricated or constructed of material providing any suitable range of light transmittance which is preferably sufficient to uniformly illuminate the viewing portion 122 of the transparency 104 yet which also eliminates the occurrence of bright spots in the diffuser 48.

In one embodiment, the diffuser 48 may be configured as a sheet of Plexiglas having a thickness ranging from approximately 0.030 to 0.25 inch although any thickness may be used. In general, the thickness of the sheet is preferably kept to a minimum to reduce bending stresses in the diffuser when forming to a contour and to minimize the amount of heat treatment of the diffuser 48 that may be necessary to reduce or remove residual stresses that may otherwise tend to spring the diffuser 48 back toward its initially planar or flat shape. For example, the diffuser 48 may be provided as a 0.063 inch thick sheet of material having sufficient light transmittance while minimizing the extent of heat treatment required to form the diffuser 48 in a contoured shape. However, availability and/or cost may dictate a greater material thickness such as, for example, 0.118 inch thick Plexiglas sheet which may be provided as a length and width extending continuously between the upper and lower panels 16 and between the opposing sides of the housing 14 to avoid discontinuities or interruptions in the illuminated background of the transparency 104. In the illustrated embodiment wherein the transparency 104 comprises the aircraft 100 windshield 110, the diffuser 48 may be provided as a sheet of Plexiglas having a thickness of 0.118 inch and a suitable length and width (e.g., 6 feet by 8 feet) to provide a continuous background for the transparency 104. The Plexiglas may have a visible light transmittance capability of 50% although the diffuser 48 may be constructed of any material providing any degree of light transmittance.

Referring to FIGS. 4-5, shown is the diffuser 48 which may be fixedly mounted to the housing 14 and is preferably disposed in spaced relation to the light source 54 indicated by diffuser gap 52. In this regard, the diffuser 48 is preferably spaced away from the light source 54 to avoid excessive heating which could damage the diffuser 48 and/or the transparency 104. Furthermore, spacing the diffuser 48 away from the light source 54 may eliminate the occurrence of bright spots in the diffuser 48. In one embodiment, the diffuser 48 may be spaced away from the light source 54 at a diffuser gap 52 of approximately 1 inch although the diffuser 48 and the light source 54 may be spaced at diffuser gaps 52 of any size.

Referring to FIGS. 2, 3 and 5, shown is the housing 14 which may comprise one or more vertical frame members 20 interconnecting the upper and lower panels 16. The housing 14 may be configured for mounting the light source 54, the diffuser 48 and/or the reflector 64 in fixed or adjustable relation to one another. In an embodiment of the housing 14, upper and lower ends of the light fixtures 58 may be mounted to the panels 16 such as by mechanical fastening, bonding or other suitable means. Likewise, the reflector 64 and/or the diffuser 48 may be mounted to the panels 16 along the cutouts 18 formed in the panels 16 as best seen in FIG. 3. The housing 14 may be configured as a partially enclosed configuration in order to enable access to the interior of the housing 14 such as for access to the light fixtures 58 or electrical wiring for providing power from a power source (not shown) to the light fixtures 58. Wiring may also be provided to deliver electrical power to the image recording device 22 and/or to a processor or controller such as a personal computer or a laptop as may be used for controlling the image recording device 22.

The housing 14 may optionally include one or more power outlets 84 for providing power to auxiliary components. Additionally, one or more switches 86 may be included on an exterior portion of the housing 14 for activating the light source 54 and/or for activating or providing power to the image recording device 22. For example, the detection fixture 12 may include the pair of switches 86 mounted on the housing 14 for activating different portions of the lighting elements 56. One switch 86 may be adapted for activating the lighting elements 56 on the left side of the housing 14 while the other light switch 86 may be adapted to activate the lighting elements 56 on the right side of the housing 14.

Although shown as having a generally orthogonal shape with cutouts 18 in the upper and lower panels 16, the housing 14 may be configured in a variety of alternative configurations and is not limited to the arrangement shown. For example, it is contemplated that the housing 14 may be fabricated as a semi-monocoque structure or as an arrangement of tubular elements for mounting the lighting elements 56, reflector 64 and/or diffuser 48. In addition, it is also contemplated that the housing 14 may be fitted with wheels 78 in order to facilitate transportability to different locations such as in an assembly or maintenance facility.

Referring still to FIGS. 2-5, shown is the transparency fixture 70 for mounting the transparency 104 and the image recording device 22 in fixed relation to one another. The transparency fixture 70 may be positioned relative to the diffuser 48 such that any point on the entirety of the viewing portion 122, when viewed through the image recording device 22, has the diffuser 48 in the background. More specifically, the image recording device 22, the transparency 104 and the diffuser 48 are configured and/or positioned such that a vector 34 extending from the image recording device 22 and passing through any point in the viewing portion 122 may intersect or strike the diffuser 48.

Due to the homogeneous illumination of the diffuser 48, the defect detection system 10 is adapted to facilitate the recording of detailed photographic and/or videographic images of the viewing portion 122 of the transparency 104. Background lighting of the transparency 104 by means of the homogenously illuminated diffuser 48 facilitates illumination of relatively small defects 106 which may otherwise be invisible to laser-driven mechanisms. Furthermore, the transparency fixture 70 preferably positions the image recording device 22 such that the lens 26 may capture detailed images at the extreme upper and lower edges 124, 126 of the transparency 104 as well as detailed images at the opposing lateral edges 128 of the transparency 104. For example, in the aircraft 100 windshield 110 illustrated in FIG. 2, the nose 130 of the windshield 110 defines the upper edge 124 and the arch member 120 defines the lower edge 126 of the windshield 110. The extreme opposing lateral edges 128 are likewise defined by intersections of the arch member 120 with the transparency frame 116.

Although the transparency 104 is illustrated as an aircraft 100 windshield 110, the defect detection system 10 as disclosed herein may be adapted for detecting optical defects 106 in any transparency 104 of any size, shape and configuration. Furthermore, the defect detection system 10 as disclosed herein is not limited to inspection of transparencies 104 having a contoured or curved shape. For example, it is contemplated that the defect detection system 10 and, more particularly, the diffuser 48 may be adapted to facilitate optical inspection of generally planar, flat or slightly curved transparencies 104 such that the diffuser 48 may be provided in a planar shape. Likewise, for planar transparencies 104, the reflector 64 and/or light source 54 may also be configured complementary to the diffuser 48. Furthermore, although the detection fixture 12 illustrates the transparency 104 as being mounted in relation to the image recording device 22, it is contemplated that the image recording device 22 may be mounted to the housing 14. Likewise, the detection fixture 12 may be altogether eliminated and the transparency 104 may be simply positioned in relation to the diffuser 48 and image recording device 22 such that any vector 34 passing through the lens 26 of the image recording device 22 and extending through the viewing portion 122 of the transparency 104 strikes or intersects the diffuser 48. In this regard, the vectors 34 as shown in FIGS. 4 and 5 represent the extent of what is visible through a given lens having a given field of view.

Referring to FIG. 4, the transparency fixture 70 may be configured such that the image recording device 22 may be mounted on a camera mount 42. The image recording device 22 may be positioned such that an optical axis 28 of the lens 26 is located approximately midway along a height 114 of the transparency 104 in order to facilitate inspection of extreme upper and lower edges 124, 126 of the viewing portion 122 with sufficient resolution. In this regard, the image recording device 22 is preferably provided with a vertical field of view 30 that encompasses the upper and lower edges 124, 126. As can be seen in FIG. 4, the vectors 34 extending from the lens 26 and passing through the upper and lower edges 124, 126 of the viewing portion 122 intersect the diffuser 48. As may be appreciated, the area of the transparency 104 that is intersected by the horizontally-oriented optical axis 28 may be imaged with an optimal level of resolution as compared to the remainder of the transparency. The vertical field of view 30 for the image recording device 22 as shown in FIG. 4 is indicated as being approximately 175° due to interference with an offset arm 36 and vertical arm 38 which collectively support the image recording device 22. However, the vertical field of view 30 may extend through 180° although the image recording device 22 may define other values for the field of view.

Referring to FIG. 5, the image recording device 22 also defines a horizontal field of view which, depending upon the focal length of the lens 26, may extend through 180° or larger. However, rotation of the image recording device 22 about the axis of rotation 88 along a rotation direction 90 increases the horizontal field of view 32 up to 360° and slightly beyond depending upon the rotational capability of the image recording device 22. For the transparency 104 configuration shown in FIG. 5, total rotation of the image recording device 22 along the direction of rotation 90 may be limited to 225°. Such limited rotation of the image recording device 22 in combination with a static 180° field of view of a suitable fisheye lens 26 may be sufficient to capture an entirety of the viewing portion 122 which extends between the transparency frame 116 on opposite sides of the transparency 104. With a rotation of 360°, the image recording device 22 would provide an essentially spherical field of view.

The image recording device 22 may also be adapted to be translated in order to image a desired object. For example, the image recording device 22 may be adapted to be moved vertically, horizontally, diagonally or any combination thereof in order to record images of an object such as a transparency 104. Likewise, the image recording device 22 may be adapted to be translated in combination with rotation in order to facilitate imaging of an object such as a transparency 104. In this regard, the image recording device 22 may be adapted to be moved in any manner including rotation, translation, tilt and roll and any other movement or combination of movements during imaging of a transparency 104 of other object. For example, for imaging an object of relatively large height but narrow width, the image recording device 22 may be adapted to be translated vertically such as from a bottom of the object to a top of the object during high-speed imaging of the object. For a relatively flat object having relatively large width but small height, the image recording device 22 may be adapted to be translated horizontally from one end to an opposite end of the object during high-speed imaging thereof. Furthermore, for objects the fall outside the maximum field of view of the lens, a combination of incremental imaging steps may be required to capture the entirety of the object following by post-processing to stitch together the multiple images to create a single panoramic image.

The image recording device 22 may be configured as any device of sufficiently high resolution and which may be rotatable about an axis. For example, the image recording device 22 may be configured as a panoramic camera 24 such as that which is commercially available from Panoscan, Inc. of Van Nuys, Calif. and which is commercially known as the Panoscan MK-3 camera. When fitted with a wide-angle lens 26, the image recording device 22 may be capable of recording a 360° panoramic image of the transparency 104. Detection of the optical defects 106 such as carbon particulates may be pinpointed on a pixel-by-pixel basis when the image is compared to a baseline image known to be devoid of such defects 106. A defect-free baseline image may be recorded by scanning the diffuser 48 with an image recording device 22 having the same lens 26 and using the same light source 54, diffuser 48 and/or reflector 64 setup that is used to record images of a transparency 104. Stored or real-time baseline images can be compared on a pixel-by-pixel basis to stored or real-time images of the inspected transparency 104 in order to detect and record the location and size of potential optical defects 106.

The image recording device 22 may comprise any suitable still camera 24 or video camera 24 and any digital or analog camera 24 and may be fitted with any lens 26 of any focal length. Furthermore, the image recording device 22 is not limited to being mounted on a rotatable base 40 but may be configured as a plurality of cameras 24 to collectively record images of a transparency 104 or of other objects. Even further, the image recording device 22 is preferably positioned such that the optical axis 28 is positioned approximately midway along a height 114 of the transparency 104 between the upper edge 124 and lower edge 126 (i.e., from the nose 130 to the arch member 120). However, the image recording device 22 may also be height-adjustable to allow for scanning of transparencies 104 and other objects that may be larger than that which can be encompassed by the vertical field of view 30 of the lens 26. For example, the image recording device 22 may be positionable at an upper position and at a lower position (not shown) to allow for recording of a panoramic image of an upper portion of the transparency 104 followed by panoramic imaging of a lower portion of the transparency 104 after which the transparency 104 images can be combined by stitching together the images recorded at each location. The ability to adjust the height of the image recording device 22 may increase the resolution of the transparency 104 images at upper and lower locations thereof.

Referring still to FIGS. 4-5, the image recording device 22 may be mounted to the transparency fixture 70 by means of the camera mount 42 illustrated in the Figures as being mounted on a mounting plate 72. A base 40 of the image recording device 22 may include a motorized mechanism for facilitating rotation of the image recording device 22 about the axis of rotation 88. As was earlier indicated, the image recording device 22 may be mounted such that the optical center of the lens 26 is coincident with the axis of rotation 88 as shown in FIG. 5 such that, during rotation of the image recording device 22 about the axis of rotation 88, the optical center is essentially stationary. However, the image recording device 22 may be configured such that the optical center rotates during rotation of the image recording device 22.

In one embodiment, the image recording device 22 preferably has a resolution sufficient to record defects 106 having a cross-sectional width of at least as small as about 0.010 inch over an entirety of the viewing portion 122 of the transparency 104. For example, the camera 24 may have a vertical resolution of up to at least about 9,000 pixels and a horizontal resolution of up to at least about 65,000 pixels depending upon the angular rotation of the camera. However, the image recording device 22 may be provided in any resolution capability sufficient to record defects of a given size. Ideally, the image recording device 22 is configured as a digital camera 24 in order to allow for the generation of digital records of defect 106 size and location as well as the ability to identify defects 106 having sizes as small at least about 0.030 inch and more preferably at least as small as about 0.010 inch or smaller. For example, the image recording device 22 may have a resolution sufficient to record defects as small as 0.005 inch or smaller. Additionally, the camera 24 is preferably provided as a high-speed digital camera 24 to reduce the amount of time required to scan and record images of large transparencies 104. Advantageously, the defect detection system 10 facilitates illumination and detection of defects 106 which may otherwise be invisible to laser-driven mechanisms for defect 106 recording. Furthermore, the contouring or shaping of the diffuser 48 complementary to the contour of the transparency 104 facilitates reliable, accurate detection of relatively small optical defects 106 along and between the extreme upper and lower edges 124, 126 and along and between the opposing lateral edges 128 of the transparency 104.

Referring still to FIGS. 4-5, the transparency fixture 70 is configured for supporting the transparency 104 such that the transparency 104 is generally vertically-oriented in order to equalize the distance from the camera 24 to the transparency 104 at the upper and lower edges 124, 126. In this manner, the upper and lower edges 124, 126 of the viewing portion 122 may be imaged with generally equivalent levels of resolution. Ideally, the transparency 104 is also preferably mounted on the transparency fixture 70 such that the transparency 104 is generally oriented in parallel relation to or in alignment with the diffuser 48 such that the viewing portion 122 of the transparency 104 is generally homogenously or substantially uniformly illuminated by the diffuser 48.

As indicated above, the positioning of the transparency 104 relative to the camera 24 and diffuser 48 is preferably, but optionally, such that for any vector 34 that projects or extends from the lens 26 and then passes through any location of the viewing portion 122 of the transparency 104, the vector 34 will strikes or intersects the diffuser 48. Toward this end, the transparency 104 may be mounted on a pair of shim blocks 76 or other suitable height-adjustable mechanism in order to facilitate a generally vertical orientation of the transparency 104. The transparency 104 may be fixedly secured to the transparency fixture 70 using temporary mechanical fasteners 74 inserted through transparency mounting holes 118 and into the transparency frame 116. Although the transparency 104 is illustrated in FIG. 5 as being secured to the transparency fixture 70 by a pair of temporary mechanical fasteners 74 such as Cleco fasteners, any number of mechanical fasteners 74 and associated bracketry may be provided in order to fixedly secure the transparency 104 to prevent movement during inspection. For example, a third mechanical fastener 74 may be extended through one or more transparency mounting holes 118 in the arch member 120 at the crest of the transparency 104 as best seen in FIG. 4. However, the transparency 104 may be supported on the transparency fixture 70 without the aid of mechanical or other attachment means.

The transparency fixture 70 is illustrated as comprising a set of vertical frames 80 interconnecting a set of horizontally oriented horizontal panels 82. However, the transparency fixture 70 may be configured in a variety of alterative arrangements suitable for fixedly securing the image recording device 22 and the transparency 104 to the transparency fixture 70. Additionally, the transparency fixture 70 may be fitted with wheels 78 or other mechanism to facilitate movement of the transparency 104 relative to the detection fixture 12. However, as was indicated above, the transparency 104 may be mounted to the detection fixture 12 such that the transparency fixture 70 may be omitted.

It should also be noted that although the transparency fixture 70 illustrates the transparency 104 in a nose-up configuration, the transparency 104 may be oriented in any alternative orientation sufficient to allow imaging of the transparency 104 by the image recording device 22. Furthermore, the defect detection system 10 may be configured in any arrangement wherein the digital camera 24 may record images of the transparency 104 by means of rotation about a vertically-oriented axis of rotation 88 and/or about a horizontally-oriented axis of rotation or about axes oriented in other directions. Furthermore, the defect detection system 10 is not to be construed to be limited to inspecting a single transparency 104 at one time but may be configured to inspect multiple (i.e., two or more) transparencies 104 or other objects during a single imaging operation. Although described above with reference to inspecting transparencies 104, it is also contemplated that the defect detection system 10 may be employed for inspecting non-transparent objects or objects through which visible light is not passable. In this regard, the image recording device 22 may be employed to record panoramic images of objects having a curved shape.

Figure 6:
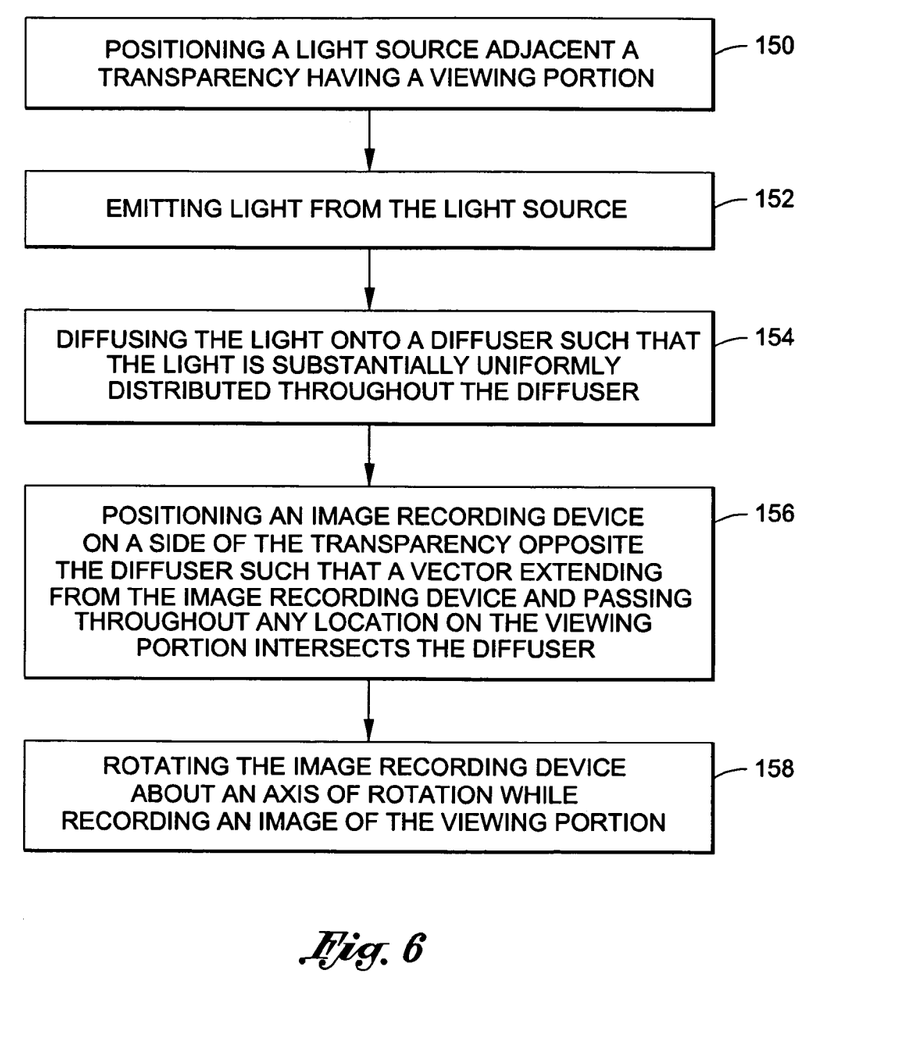
FIG. 6 is a flow chart representing a methodology of detecting optical defects in the transparency.

Referring to FIG. 6, shown is a methodology for detecting optical defects 106 in a transparency 104 or other object. As indicated above, the transparency 104 may include a viewing portion 122 surrounded by the transparency frame 116. The method may comprise step 150 including positioning the light source 54 adjacent the transparency 104. As was earlier indicated, the light source 54 may be configured in a variety of alternative arrangements including, but not limited to, an arcuately-arranged set of fluorescent lamps 62 oriented in spaced parallel relation to one another. The light source 54 may be located in spaced arrangement relative to the transparency 104 to avoid excessive radiative heating of the transparency 104.

Step 152 may comprise emitting light from the light source 54 such that the light is incident upon the diffuser 48. A reflector 64 may be included behind the light source 54 as shown in FIGS. 3-5 in order to increase the amount and/or intensity of light that is incident upon the diffuser 48. As indicated above, the reflector 64 is preferably configured to reflect or redirect the light onto the diffuser 48 in such a manner as to avoid shadows or non-uniform illumination of the diffuser 48 and to provide an evenly lit background against which the transparency 104 may be imaged by the image recording device 22. In order to avoid excess heat buildup in the diffuser 48, the diffuser 48 may be positioned at a spaced distance away from the light source 54 as defined by diffuser gap 52 shown in FIGS. 4-5. The spacing of the diffuser 48 from the light source 54 further facilitates a substantially homogenous illumination of the diffuser 48 by eliminating shadows, hot spots and/or bright spots in the diffuser 48.

Step 154 comprises diffusing the light onto the diffuser 48 such that the light is substantially uniformly diffused or distributed throughout the diffuser 48 for uniform imaging of the transparency 104. In a preferable but optional embodiment, the diffuser 48 may be configured to transmit about 50% of the light that is emitted by the light source 54 although the diffuser 48 may be configured to transmit any amount of light that sufficiently illuminates or backlights the transparency 104. The diffuser 48 may be formed of a variety of different materials without limitation including polymeric materials such as acrylic or Plexiglas sheet although any material may be used. The material is preferably selected to provide the desired light transmission characteristics. The diffuser 48 may optionally be formed as a combination of materials or as an assembly that is configured to provide a uniformly-illuminated background for viewing the transparency 104.

Step 156 comprises positioning the image recording device 22 on a side 108 of the transparency 104 that is opposite from the image recording device 22 such that a vector 34 passing through any portion of the viewing portion 122 will intersect or strike the diffuser 48 as shown in FIGS. 4-5. In this regard, the diffuser 48 is preferably contoured complementary to the contour of the transparency 104 such that the entirety of the viewing portion 122 is uniformly backlit by the diffuser 48. Likewise, the light source 54 and/or the reflector 64 are preferably arranged such that any area of the viewing portion 122 that is viewable through the lens 26 will be backlit by a uniformly-illuminated area of the diffuser 48 including backlighting by the perimeter edges of the diffuser 48. Toward this end, the diffuser 48 may be of a larger size than the transparency 104.

The method of imaging the transparency 104 may comprise positioning the image recording device 22 at a suitable location to maximize the resolution at all areas of the transparency 104. For example, the image recording device 22 may be positioned midway along a height of the transparency 104 to equalize the resolution at upper and lower edges 124, 126. The image recording device 22 may be positioned at a location that equalizes the resolution at lateral edges 128 of the transparency 104. The image recording device 22 is preferably positioned such that at least a part of the viewing portion 122 may be captured within the field of view 30, 32 of the lens 26 when the image recording device 22 is stationary. For relatively large transparencies having areas that normally fall outside of the field of view 30, 32 (i.e., when the camera is stationary), imaging of the entirety of the viewing portion 122 may require moving the image recording device 22 while recording images. For the example of the transparency 104 shown in FIG. 4, the upper and lower edges 124, 126 of the viewing portion 122 fall within the field of view 30 of the image recording device 22.

However, as shown in FIG. 5, the lateral edges 128 of the viewing portion 122 fall outside of the field of view 30, 32 (i.e., when the camera is stationary) and therefore, movement of the image recording device 22 is required in order to image the entirety of the viewing portion 122 from one lateral edge 128 to the opposite lateral edge 128. For contoured or curved transparencies 104, step 158 may comprise rotating the image recording device 22 about the axis of rotation 88 while recording images of the viewing portion 122 as shown in FIG. 5. However, the image recording device 22 may be moved in any suitable manner in order to image the entirety of the viewing portion 122. Movement of the image recording device 22 may comprise translation, rotation, roll, tilt or other movements and combinations thereof. Movement of the image recording device 22 may further comprise rotation of the image recording device 22 about at least one axis of rotation such as the axis of rotation 88 illustrated in FIG. 4 which is shown as a vertical axis of rotation. However, the image recording device 22 may be rotated about other axes of rotation. In addition, the image recording device 22 may be translated (e.g., moved vertically, horizontally, laterally, etc.) or may be translated in combination with rotational movement while recording images. As mentioned earlier, multiple images of different areas of the transparency 104 may be stitched together or otherwise assembled to create a single composite or panoramic image of the transparency 104.

As indicated above, the diffuser 48 may have a contour that is preferably, but optionally, formed complementary to the contour of the transparency 104. The image recording device 22 is preferably positioned in relation to the transparency 104 and the diffuser 48 such that rotation of the image recording device 22 about the axis of rotation 88 allows for minimal variation in the distance from the lens 26 to the transparency 104 between upper and lower edges 124, 126 such that the quality of the image (i.e., the resolution) is generally equal at the upper and lower edges 124, 126. Likewise, the image recording device 22 is preferably positioned in relation to the transparency 104 such that the resolution at the opposing lateral edges 128 is generally equal. However, it is contemplated that the image recording device 22 may be positioned in relation to the transparency 104 such that resolution is greater at certain areas of the transparency 104 as compared to other areas. The optical defect detection system 10 is preferably arranged to allow for recording of defects having a width at least as small as about 0.010 inch or smaller over an entirety of the viewing portion 122 of the transparency 104. Toward this end, the image recording device 22 may be configured as a digital camera such that digital records of the defect may be located and documented.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. An optical defect detection system for recording an image of a transparency having a contour, comprising:
    a plurality of lighting elements configured to emit light and arranged in an arcuate cross-sectional profile substantially similar to the transparency cross-sectional profile, each one of the lighting elements having a tubular shape and extending in a lengthwise direction along a length of the transparency, the plurality of lighting elements being arranged in an arcuate pattern;
    a diffuser interposed between the lighting elements and the transparency and being a physically separate component from the lighting elements and the transparency and providing a background for recording images of the transparency;
    the diffuser having an arcuate cross-sectional profile being substantially similar to the transparency cross-sectional profile;
    the arcuate cross-sectional profile of the diffuser and the light source being configured such that the transparency is substantially uniformly backlit by the combination of the lighting elements and the diffuser;

a reflector positioned on a side of the lighting elements opposite the diffuser and being configured to reflect light emitted by the lighting elements toward the diffuser; and an image recording device positioned on a side of the transparency opposite the diffuser such that no intervening elements are located between the image recording device and the transparency, the image recording device being configured to record the image of the substantially uniformly backlit transparency for detection of optical defects in the transparency.

2. The defect detection system of claim 1 wherein:
the transparency having a viewing portion;
the image recording device, the transparency and the diffuser being configured such that a vector that extends from the image recording device and which passes through any point on the viewing portion will intersect the diffuser.

3. The defect detection system of claim 1 wherein:
the transparency has a viewing portion defining upper and lower edges;
the image recording device having a vertical field of view encompassing the upper and lower edges.

4. The defect detection system of claim 1 wherein:
the transparency has a viewing portion defining opposing lateral edges;
the image recording device being configured as a panoramic camera rotatable about an axis of rotation to record the viewing portion between and including the opposing lateral edges.

5. The defect detection system of claim 1 wherein:
the image recording device is configured to record optical defects having a width at least as small as about 0.010 inch.

6. The defect detection system of claim 1 wherein:
the diffuser is configured to transmit at least about 50% of the light emitted by the lighting elements.

7. The defect detection system of claim 1 wherein:
the image recording device comprises at least one of the following: a digital camera, a video camera.

8. The defect detection system of claim 1 wherein:
the transparency comprises at least one of an aircraft canopy and an aircraft windshield.

9. An optical defect detection system for recording an image of a transparency having a viewing portion with opposing lateral edges, the detection system comprising:
a plurality of lighting elements configured to emit light and arranged in an arcuate cross-sectional profile substantially similar to the transparency cross-sectional profile, each one of the lighting elements having a tubular shape and extending in a lengthwise direction along a length of the transparency, the plurality of lighting elements being arranged in an arcuate pattern;
a diffuser interposed between the lighting elements and the transparency and being a physically separate component from the lighting elements and the transparency and providing a background for recording images of the transparency;
the diffuser having an arcuate cross-sectional profile being substantially similar to the transparency cross-sectional profile;
the arcuate cross-sectional profile of the diffuser and the lighting elements being configured such that the transparency is substantially uniformly backlit by the combination of the lighting elements and the diffuser;
a reflector positioned on a side of the lighting elements opposite the diffuser and being configured to reflect light emitted by the lighting elements toward the diffuser; and
an image recording device positioned on a side of the transparency opposite the diffuser such that no intervening elements are located between the image recording device and the transparency, the image recording device being rotatable about an axis of rotation to record a horizontal field of view encompassing the viewing portion between and including the opposing lateral edges;
the image recording device, the transparency and the diffuser being configured such that a vector extending from the image recording device and passing through any point on the viewing portion intersects the diffuser;
the image recording device being configured to record the image of the substantially uniformly backlit transparency for detection of optical defects in the transparency.

10. The defect detection system of claim 9 wherein:
the transparency has a viewing portion defining upper and lower edges;
the image recording device having a vertical field of view encompassing the upper and lower edges.

11. The defect detection system of claim 9 wherein:
the image recording device is configured to record optical defects having a width at least as small as about 0.010 inch.

12. The defect detection system of claim 9 wherein:
the diffuser is configured to transmit at least about 50% of the light emitted by the lighting elements.

13. The defect detection system of claim 9 wherein:
the image recording device comprises at least one of the following: a digital camera, a video camera.

14. A method of detecting optical defects in a transparency having a viewing portion, the method comprising the steps of:
positioning a plurality of lighting elements adjacent the transparency, the lighting elements being arranged in an arcuate cross-sectional profile substantially similar to the transparency cross-sectional profile, each one of the lighting elements having a tubular shape and extending in a lengthwise direction along a length of the transparency, the plurality of lighting elements being arranged in an arcuate pattern;
emitting light from the lighting elements;
diffusing the light onto a diffuser for substantially uniformly backlighting the transparency, the diffuser being a physically separate component from the lighting elements and the transparency and providing a background for recording images of the transparency, the diffuser having an arcuate cross-sectional profile being substantially similar to the transparency cross-sectional profile, the arcuate cross-sectional profile of the diffuser and the lighting elements being configured such that the transparency is substantially uniformly backlit by the combination of the lighting elements and the diffuser;
reflecting the light toward the diffuser using a reflector positioned on a side of the lighting elements opposite the diffuser;
positioning an image recording device on a side of the transparency opposite the diffuser such that no intervening elements are located between the image recording device and the transparency and such that a vector that extends from the image recording device and which passes through any location on the transparency will intersect the diffuser; and
recording an image of the substantially uniformly backlit transparency for detection of optical defects in the transparency.

15. The method of claim 14 further comprising the step of:
moving the image recording device while recording the image of the viewing portion.

16. The method of claim 15 wherein the step of moving the image recording device comprises:
   rotating the image recording device about at least one axis of rotation while recording the image of the viewing portion.

17. The method of claim 16 wherein:
   the axis of rotation is a vertical axis of rotation.

18. The method of claim 14 further comprising the step of:
   transmitting at least about 50% of the light through the diffuser.

19. The method of claim 14 further comprising the step of:
   positioning the image recording device approximately midway along a height of the transparency.

20. The method of claim 14 further comprising the step of:
   recording optical defects having a width at least as small as about 0.010 inch.

* * * * *